United States Patent
Chiu et al.

(10) Patent No.: US 10,767,004 B1
(45) Date of Patent: Sep. 8, 2020

(54) TRICYCLODECANE DIMETHANOL COMPOSITION AND USES THEREOF

(71) Applicants: DAIREN CHEMICAL CORPORATION, Taipei (TW); CHANG CHUN PLASTICS CO., LTD., Taipei (TW)

(72) Inventors: Shih-Feng Chiu, Taipei (TW); Ching-Jui Huang, Taipei (TW); Hsing-Yun Wang, Taipei (TW); June-Yen Chou, Taipei (TW)

(73) Assignees: DAIREN CHEMICAL CORPORATION, Taipei (TW); CHANG CHUN PLASTICS CO., LTD., Taipei (TW)

( * ) Notice: Subject to any disclaimer, the term of this patent is extended or adjusted under 35 U.S.C. 154(b) by 0 days.

(21) Appl. No.: 16/791,221

(22) Filed: Feb. 14, 2020

Related U.S. Application Data

(60) Provisional application No. 62/960,382, filed on Jan. 13, 2020.

(51) Int. Cl.
*C08G 63/12* (2006.01)
*C08G 63/02* (2006.01)
*C08G 63/00* (2006.01)
*C08G 63/137* (2006.01)
*C07C 31/27* (2006.01)

(52) U.S. Cl.
CPC .......... *C08G 63/137* (2013.01); *C07C 31/278* (2013.01); *C07C 2603/66* (2017.05)

(58) Field of Classification Search
CPC .......... C08G 63/12; C08G 63/02; C08G 63/00
USPC .............................. 528/296, 272, 271; 520/1
See application file for complete search history.

(56) References Cited

U.S. PATENT DOCUMENTS

| 6,365,782 B1 * | 4/2002 | Nakamura ............. C07C 29/16 568/444 |
| 10,538,472 B1 * | 1/2020 | Chou ................... C07C 29/141 |
| 2012/0203026 A1 | 8/2012 | Kawakami et al. |

FOREIGN PATENT DOCUMENTS

| CN | 1636950 A | 7/2005 |
| CN | 1890203 A | 1/2007 |
| CN | 101353419 A | 1/2009 |
| CN | 101497561 A | 8/2009 |
| GB | 1170226 A | 11/1969 |
| JP | H11100339 A | 4/1999 |
| JP | 2003146931 A | 5/2003 |
| WO | 1986003737 A1 | 7/1986 |
| WO | 2018014746 A1 | 1/2018 |

OTHER PUBLICATIONS

Tricyclodecanedimethanol—Tech Data, published Aug. 2005 (Year: 2005).*
International Search Report and Written Opinion for WO Application No. PCT/CN2020/075315, dated May 15, 2020.

* cited by examiner

*Primary Examiner* — Jessica Whiteley
(74) *Attorney, Agent, or Firm* — Nixon Peabody LLP; Thomas P. Pavelko

(57) ABSTRACT

Compositions containing Tricyclodecane Dimethanol (TC-CDM) and at least a second component, wherein the composition is characterized in a gas chromatography (GC) analysis, wherein the TCDDM is eluted at a retention time ranging from 12.4 minutes to 13 minutes, the second component is eluted at a retention time ranging from 11.8 minutes to 12.4 minutes, and the ratio of the area of elution peaks indicating the second component compared to the area of the elution peaks of the TCCDM is between 0.001:1 and 0.04:1. Useful products of the composition include polymers and optical materials.

17 Claims, 4 Drawing Sheets

TRICYCLODECANE DIMETHANOL COMPOSITION AND USES THEREOF

CROSS-REFERENCE TO RELATED APPLICATIONS

This application includes a claim of priority under 35 U.S.C. § 119(e) to U.S. provisional patent application No. 62/960,382, filed Jan. 13, 2020, the entirety of which is hereby incorporated by reference.

FIELD OF THE INVENTION

The present disclosure relates to a new composition containing tricyclodecane dimethanol, suitable as a raw material for making transparent optical materials.

BACKGROUND

All publications herein are incorporated by reference to the same extent as if each individual publication or patent application was specifically and individually indicated to be incorporated by reference. The following description includes information that may be useful in understanding the invention. It is not an admission that any of the information provided herein is prior art or relevant to the presently claimed invention, or that any publication specifically or implicitly referenced is prior art.

Optical materials or polymeric materials used for electronic parts and the like are often required to have high transparency. That is at least due to processing amenability such as allowing for a wide range of light sources for light signal. For example, a light source with a low wavelength range, e.g., blue laser, UV laser, and the like, requires an optical material has high transparency. As such, an aromatic polyester that has poor light transmission or UV resistance is difficult to be applied to such fields.

While various polyester resins can be molded into a film, a sheet, an elastomer, a fiber, a tube, a container or the like and used in a broad field, it is important to include an appropriate comonomer in the making to improve the transparency such as anti-yellowing properties of the polyester resins. Similarly, polyester carbonate, polycarbonate, acrylate resin, and methacrylate resin, or the like can be used as various optical materials, and including an appropriate comonomer to improve transparency of the polymers would be desirable.

An object of the present application is to provide compositions of tricycloalkane dimethanol with specific components, which are suitable as raw materials for manufacturing downstream products with improved optical properties.

SUMMARY OF THE INVENTION

The following embodiments thereof are described and illustrated in conjunction with systems, articles of manufacture, compositions, and processes which are meant to be exemplary and illustrative, not limiting in scope.

Compositions containing tricyclodecane dimethanol (TCDDM) are provided, which have specific components and can be used to produce polymers or resins for applications such as making optical materials.

In some embodiments, the claimed composition includes a first component which is a TCDDM, and a second component, wherein when the composition is characterized in a gas chromatography (GC) analysis, the second component is eluted at a retention time ranging from 11.8 minutes to 12.4 minutes, and the ratio of the area of elution peaks indicating the second component (e.g., peaks within the retention time range between 11.8 minutes and 12.4 minutes) compared to the area of elution peaks indicating the TCDDM (e.g., peaks within the retention time range between 12.4 minutes and 13 minutes) is between 0.001:1 and 0.04:1. In various embodiments, the TCDDM is eluted at a retention time ranging from 12.4 minutes to 13 minutes in the GC analysis.

In some embodiments, the composition's second component has a fragmentation pattern comprising one or more peaks at mass-to-charge ratio (m/z) comprising 31, 41, 67, 79, 91, 93, 119, 149, 167, or a combination thereof, when the composition is characterized in a gas chromatography-mass spectrometry (GC/MS) analysis. In further embodiments, the composition's second component has a fragmentation pattern comprising at least peaks at m/z of 149 and 167. In further embodiments, the second component has a retention time ranging from 15.0 minutes to 16.5 minutes in one GC/MS analysis, whereas the TCDDM has a retention time ranging from 16.5 minutes and 17.5 minutes in the GC/MS analysis.

In some embodiments, a composition includes a first component which is a TCDDM, a second component as described above, and a third component which is a compound of formula (X):

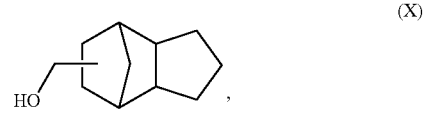

wherein in a GC analysis, the ratio of the area of the elution peak indicating the compound of formula (X) compared to the area of the elution peak indicating the TCDDM is between 0.00005:1 and 0.005:1. In one embodiment, the composition's third component is eluted at a retention time ranging from 10.8 minutes to 11.2 minutes in the GC analysis.

In some embodiments, the area under curve of elution peaks indicating the TCDDM compared to a total area of elution peaks of the composition (solvent not included) is in a ratio of 0.95:1 or greater.

Some embodiments provide the second component is one or a mixture of compounds represented by formula (XI):

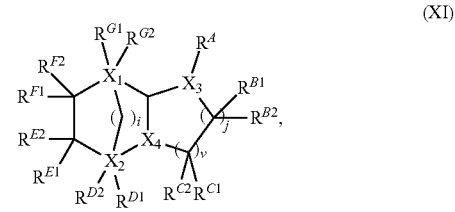

wherein $X_1$ is C; $X_2$ is C; i=1 or 0; j=1 or 0; v=1 or 0; and if i=1, then j=v=0, $R^{B1}$, $R^{B2}$, $R^{C1}$, $R^{C2}$, $R^{D1}$ and $R^{G1}$ are absent, $(X_3 \_R^A)$ is a linear or branched $C_4$ alkyl alcohol, $X_4$ is $CH_2$ or $CH(CH_2OH)$, and if $X_4$ is $CH_2$, then one of $R^{D2}$, $R^{E1}$, $R^{E2}$, $R^{F1}$, $R^{F2}$ and $R^{G2}$ is $CH_2OH$ whereas the other five of $R^{D2}$, $R^{E1}$, $R^{E2}$, $R^{F1}$, $R^{F2}$ and $R^{G2}$ are H;

if $X_4$ is $CH(CH_2OH)$, then $R^{D2}$, $R^{E1}$, $R^{E2}$, $R^{F1}$, $R^{F2}$ and $R^{G2}$ are H; and if i=0, then j=v=1, $X_3$ is CH, $X_4$ is CH, one of $R^A$, $R^{B1}$, $R^{B2}$, $R^{C1}$ and $R^{C2}$ is $CH_2OH$ whereas the other four of $R^A$, $R^{B1}$, $R^{B2}$, $R^{C1}$ and $R^{C2}$ are H, one of $R^{D1}$, $R^{D2}$, $R^{E1}$, $R^{E2}$, $R^{F1}$, $R^{F2}$, $R^{G1}$ and $R^{G2}$ is $CH_2OH$, another one of $R^{D1}$, $R^{D2}$, $R^{E1}$, $R^{E2}$, $R^{F1}$, $R^{F2}$, $R^{G1}$ and $R_{G2}$ is $CH_3$, whereas the other six of $R^{D1}$, $R^{D2}$, $R^{E1}$, $R^{E2}$, $R^{F1}$, $R^{F2}$, $R^{G1}$ and $R^{G2}$ are H.

Some embodiments provide the second component in the compositions comprises one or more compounds of the following formulae:

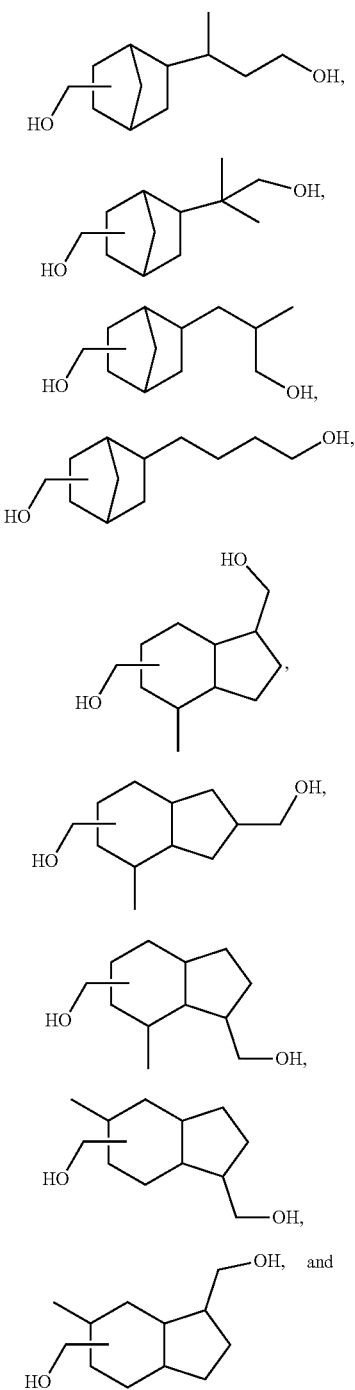

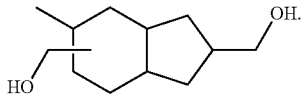

Polymers are provided which can be derived from the compositions described above. For example, a polyester, an epoxy, an acrylate, a polycarbonate or a polyurethane may be synthesized or modified to contain the composition described above. The polymers can be made into an optical material, for use in various applications such as an optical disc, a fiber or a lens.

DETAILED DESCRIPTION OF THE INVENTION

Figure 1:
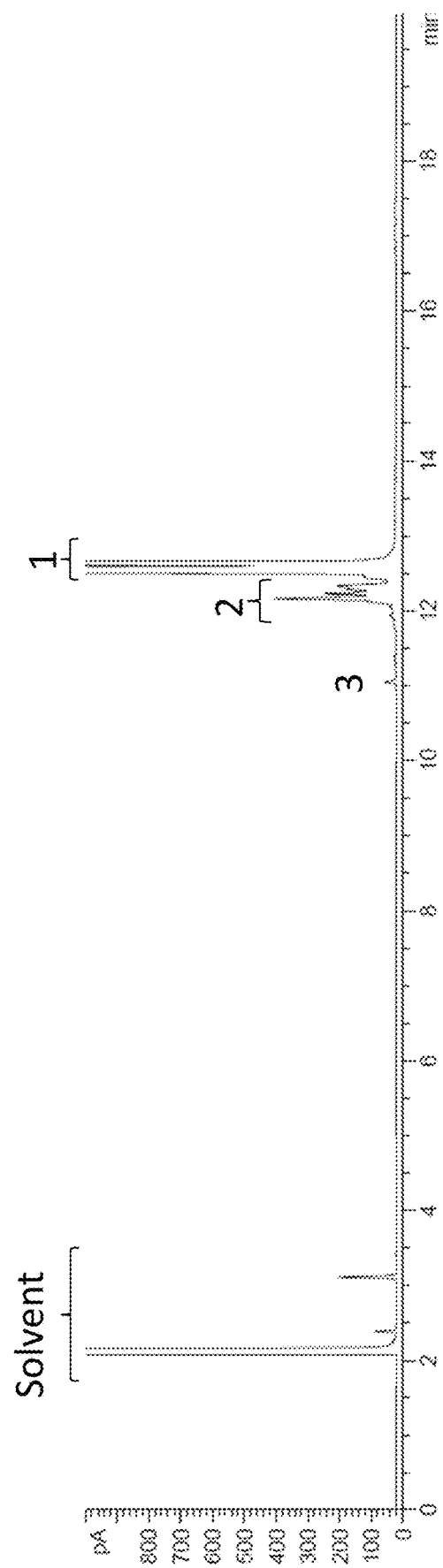
FIG. 1 is a retention time spectrum in the GC analysis of the TCDDM-based composition of Example 4.

All references cited herein are incorporated by reference in their entirety as though fully set forth. Unless defined otherwise, technical and scientific terms used herein have the same meaning as commonly understood by one of ordinary skill in the art to which this present application belongs. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this present application belongs. It should be understood that this present application is not limited to the particular methodology, protocols, and reagents, etc., described herein and as such can vary. The definitions and terminology used herein are provided to aid in describing particular embodiments, and are not intended to limit the claimed invention.

One skilled in the art will recognize many methods and materials similar or equivalent to those described herein, which could be used in the practice of the present application. Other features and advantages of the present application will become apparent from the following detailed description. Indeed, the present application is in no way limited to the methods and materials described. For convenience, certain terms employed herein, in the specification, examples and appended claims are collected here.

As used herein the term "comprising" or "comprises" is used in reference to compositions, methods, processes, articles of manufacture, systems, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having"

should be interpreted as "having at least," the term "includes" should be interpreted as "includes but is not limited to," etc.). Although the open-ended term "comprising," as a synonym of terms such as including, containing, or having, is used herein to describe and claim the present application, the invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All processes described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

The term "about" as used herein can mean plus/minus 20% of the stated value. For example, about 75° C. encompasses the range of 60° C. to 90° C.

Various embodiments of the present application provide TCDDM-based compositions suitable for preparing polyesters of high transparency or low opacity, which satisfies needs of industrial applications.

In some embodiments, when dissolved in a solvent for a GC analysis (spectrum shown in FIG. 1), a TCDDM-based composition has a first component (i.e., TCDDM) which is eluted at a retention time from 12.4 minutes to 13 minutes, and a second component which is eluted from 11.8 minutes to 12.4 minutes, and the ratio of the area of the elution peak indicating the second component compared to the area of the elution peak indicating the first component is between 0.001:1 and 0.04:1, wherein the GC analysis includes eluting the TCDDM-based composition from a BP-5 capillary column of 30 meters in length, 530 μm in inner diameter and a film thickness of 1 μm, and characterized with a liquid phase of 5% phenyl and 95% dimethyl-polysiloxane and a carrier gas of nitrogen flown at 5 mL/min for initial 11 minutes followed by a stepping flow rate from 5 mL/min to 10 mL/min at a rate increment of 1 mL/min, (and subsequently maintained at 10 mL/min until end of GC analysis), under a stepping temperature in a sequence of 50° C. for 1 minutes, then increasing temperature from 50° C. to 180° C. at an increment of 15° C./min, then increasing temperature from 180° C. to 250° C. at an increment of 30° C./min, followed by 250° C. for 8 minutes, wherein an inlet temperature is 250° C., a sample injection volume of the composition is 2 μL, and a detector is a flame ionization detector operated at 300° C. In various embodiments, an area of elution peak(s) indicating a component is defined as the area in a GC spectrum that is under an elution curve (e.g., can be one singlet, duplet, triplet, etc peak or multiple peaks, so long as within a specified retention time range of the component) and above a baseline typically determined by the GC operating system.

In one embodiment, a composition is characterized by the GC analysis, wherein the ratio of the area of the elution peaks indicating the second component compared to the area of the elution peaks indicating the first component is between 0.001:1 and 0.04:1.

In another embodiment, a composition is characterized by the GC analysis, wherein the ratio of the area of the elution peaks indicating the second component compared to the area of the elution peaks indicating the first component is between 0.001:1 and 0.039:1.

In another embodiment, a composition is characterized by the GC analysis, wherein the ratio of the area of the elution peaks indicating the second component compared to the area of the elution peaks indicating the first component is between 0.0012:1 and 0.039:1.

In yet another embodiment, a composition is characterized by the GC analysis, wherein the ratio of the area of the elution peaks indicating the second component compared to the area of the elution peaks indicating the first component is between 0.0012:1 and 0.027:1.

In some embodiments, a composition when characterized by the GC analysis has a ratio of the area of the elution peaks indicating the second component compared to the area of the elution peaks indicating the first component being 0.001:1, 0.002:1, 0.003:1, 0.004:1, 0.005:1, 0.006:1, 0.007:1, 0.008:1, 0.009:1, 0.01:1, 0.011:1, 0.012:1, 0.013:1, 0.014:1, 0.015:1, 0.016:1, 0.017:1, 0.018:1, 0.019:1, 0.02:1, 0.021:1, 0.022:1, 0.023:1, 0.024:1, 0.025:1, 0.026:1, 0.027:1, 0.028:1, 0.029:1, 0.03:1, 0.031:1, 0.032:1, 0.033:1, 0.034:1, 0.035:1, 0.036:1, 0.037:1, 0.038:1, 0.039:1, 0.04:1, or a ratio in between any two values listed.

Further embodiments of the compositions provide, when characterized by the GC analysis, the area of elution peaks of the second component relative to the total area of elution peaks from a composition excluding the solvent is between 0.001:1 and 0.04:1; or the ratio of the area of the elution peaks indicating the second component compared to the total area of the elution peaks indicating the composition (not including a solvent) is between 0.001:1 and 0.04:1. The total area of elution peaks of the composition (i.e., excluding the solvent) typically includes the area of the elution peaks indicating the first component and the area of the elution peaks indicating the second component.

In a further embodiment of the compositions, when characterized by the GC analysis, the area of elution peaks of the second component relative to the total area of elution peaks excluding that of the solvent is between 0.001:1 and 0.039:1; or in other words, the ratio of the area of the elution peaks indicating the second component compared to the total area of the elution peaks indicating the composition (not including a solvent) is between 0.001:1 and 0.039:1.

In another embodiment of the compositions, when characterized by the GC analysis, the area of elution peaks of the second component relative to the total area of elution peaks excluding that of the solvent is between 0.001:1 and 0.038:1; or in other words, the ratio of the area of the elution peaks indicating the second component compared to the total area of the elution peaks indicating the composition (not including a solvent) is between 0.001:1 and 0.038:1.

In another embodiment of the compositions, when characterized by the GC analysis, the area of elution peaks of the second component relative to the total area of elution peaks excluding that of the solvent is between 0.0012:1 and 0.038:1; or in other words, the ratio of the area of the elution peaks indicating the second component compared to the total area of the elution peaks indicating the composition (not including a solvent) is between 0.0012:1 and 0.038:1.

In yet another embodiment of the compositions, when characterized by the GC analysis, the area of elution peaks of the second component relative to the total area of elution peaks excluding that of the solvent is between 0.0012:1 and 0.027:1; or in other words, the ratio of the area of the elution peaks indicating the second component compared to the total area of the elution peaks indicating the composition (not including a solvent) is between 0.0012:1 and 0.027:1.

Yet another embodiment of the compositions provides that, when characterized by the GC analysis, the area of the elution peaks indicating the second component relative to the total area of elution peaks of a composition excluding that of the solvent is 0.001, 0.002, 0.003, 0.004, 0.005, 0.006, 0.007, 0.008, 0.009, 0.01, 0.011, 0.012, 0.013, 0.014, 0.015, 0.016, 0.017, 0.018, 0.019, 0.02, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.04, or a number in between any two values listed. Further embodiments of the compositions provide, when characterized by the GC analysis, the ratio of the area of the elution peaks indicating the second component compared to the total area of the elution peaks indicating the composition (not including a solvent) is 0.001:1, 0.002:1, 0.003:1, 0.004:1, 0.005:1, 0.006:1, 0.007:1, 0.008:1, 0.009:1, 0.01:1, 0.011:1, 0.012:1, 0.013:1, 0.014:1, 0.015:1, 0.016:1, 0.017:1, 0.018:1, 0.019:1, 0.02:1, 0.021:1, 0.022:1, 0.023:1, 0.024:1, 0.025:1, 0.026:1, 0.027:1, 0.028:1, 0.029:1, 0.03:1, 0.031:1, 0.032:1, 0.033:1, 0.034:1, 0.035:1, 0.036:1, 0.037:1, 0.038:1, 0.039:1, 0.04:1, or a ratio in between any two values listed.

The compositions of the present application, in some embodiments, have a third component which is eluted at a retention time from 10.8 minutes and 11.2 minutes in the GC analysis, wherein the ratio of the area of the elution peak indicating the third component (e.g., peak(s) within a retention time range between 10.8 minutes and 11.2 minutes) compared to the area of the elution peaks indicating the first component is between 0.00005:1 and 0.005:1.

In one embodiment of the compositions, when characterized by the GC analysis, the ratio of the area of the elution peak indicating the third component compared to the area of the elution peaks indicating the first component is between 0.00005:1 and 0.0018:1.

In one embodiment of the compositions, when characterized by the GC analysis, the ratio of the area of the elution peak indicating the third component compared to the area of the elution peaks indicating the first component is between 0.0001:1 and 0.0018:1.

In yet other embodiments of the compositions, the ratio of the area of the elution peak indicating the third component compared to the area of the elution peaks indicating the first component is 0.00005:1, 0.00006:1, 0.00007:1, 0.00008:1, 0.00009:1, 0.0001:1, 0.0002:1, 0.0003:1, 0.0004:1, 0.0005:1, 0.0006:1, 0.0007:1, 0.0008:1, 0.0009:1, 0.001:1, 0.0011:1, 0.0012:1, 0.0013:1, 0.0014:1, 0.0015:1, 0.0016:1, 0.0017:1, 0.0018:1, 0.0019:1, 0.002:1, 0.0021:1, 0.0022:1, 0.0023:1, 0.0024:1, 0.0025:1, 0.0026:1, 0.0027:1, 0.0028:1, 0.0029:1, 0.003:1, 0.0031:1, 0.0032:1, 0.0033:1, 0.0034:1, 0.0035:1, 0.0036:1, 0.0037:1, 0.0038:1, 0.0039:1, 0.004:1, 0.0041:1, 0.0042:1, 0.0043:1, 0.0044:1, 0.0045:1, 0.0046:1, 0.0047:1, 0.0048:1, 0.0049:1, 0.005:1, or a ratio in between any of the two values listed.

Further embodiments of the compositions provide, when characterized by the GC analysis, the ratio of the area of the elution peak indicating the third component compared to the total area of the elution peaks indicating a composition (not including that of the solvent) is between 0.00005:1 and 0.005:1, between 0.00005:1 and 0.0018:1, or between 0.0001:1 and 0.0018:1. Various embodiments provide that the total area of elution peaks of the composition (i.e., excluding the solvent) includes the area of the elution peaks indicating the first component, the area of the elution peaks indicating the second component and the area of the elution peak indicating the third component. In further embodiments, the ratio of the area of the elution peak indicating the third component compared to the total area of the elution peaks indicating the composition (not including that of the solvent) is 0.00005:1, 0.00006:1, 0.00007:1, 0.00008:1, 0.00009:1, 0.0001:1, 0.0002:1, 0.0003:1, 0.0004:1, 0.0005:1, 0.0006:1, 0.0007:1, 0.0008:1, 0.0009:1, 0.001:1, 0.0011:1, 0.0012:1, 0.0013:1, 0.0014:1, 0.0015:1, 0.0016:1, 0.0017:1, 0.0018:1, 0.0019:1, 0.002:1, 0.0021:1, 0.0022:1, 0.0023:1, 0.0024:1, 0.0025:1, 0.0026:1, 0.0027:1, 0.0028:1, 0.0029:1, 0.003:1, 0.0031:1, 0.0032:1, 0.0033:1, 0.0034:1, 0.0035:1, 0.0036:1, 0.0037:1, 0.0038:1, 0.0039:1, 0.004:1, 0.0041:1, 0.0042:1, 0.0043:1, 0.0044:1, 0.0045:1, 0.0046:1, 0.0047:1, 0.0048:1, 0.0049:1, 0.005:1, or a ratio in between any of the two values listed.

More embodiments of the compositions provide, when characterized by the GC analysis, the ratio of the area of the elution peaks indicating the first component compared to the total area of the elution peaks indicating the composition (not including that of the solvent) is at least 0.95:1.

In one embodiment, the ratio of the area of the elution peaks indicating the first component compared to the total area of the elution peaks indicating the composition (not including that of the solvent) is 0.95:1, 0.951:1, 0.952:1, 0.953:1, 0.954:1, 0.955:1, 0.956:1, 0.957:1, 0.958:1, 0.959:1, 0.96:1, 0.961:1, 0.962:1, 0.963:1, 0.964:1, 0.965:1, 0.966:1, 0.967:1, 0.968:1, 0.969:1, 0.97:1, 0.971:1, 0.972:1, 0.973:1, 0.974:1, 0.975:1, 0.976:1, 0.977:1, 0.978:1, 0.979:1, 0.98:1, 0.981:1, 0.982:1, 0.983:1, 0.984:1, 0.985:1, 0.986:1, 0.987:1, 0.988:1, 0.989:1, 0.99:1, 0.991:1, 0.992:1, 0.993:1, 0.994:1, 0.995:1, 0.996:1, 0.997:1, 0.998:1, 0.999:1, or a ratio in between any two of the values listed.

Suitable solvents for the compositions of the present application in a GC analysis can be one that does not adversely affect (e.g., degrade) the composition, the GC column, or the GC equipment. Exemplary solvents for the compositions in a GC analysis include, but are not limited to, methanol, isopropanol, acetone, tetrahydrofuran, or a mixture thereof.

Figure 2A:
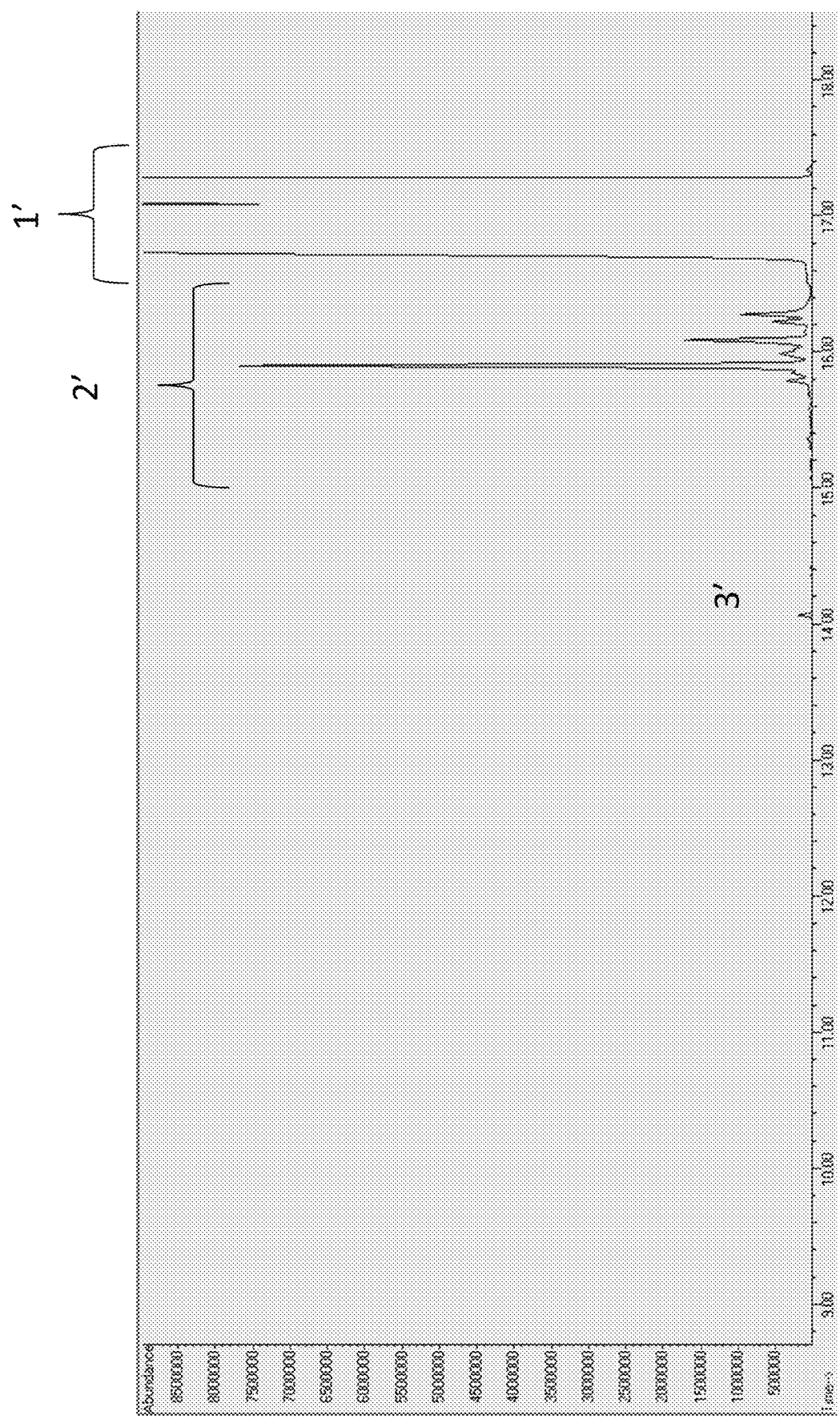
FIG. 2A and FIG. 2B are retention time spectra in the GC/MS analysis of the TCDDM-based composition of Example 4.
Figure 2B:
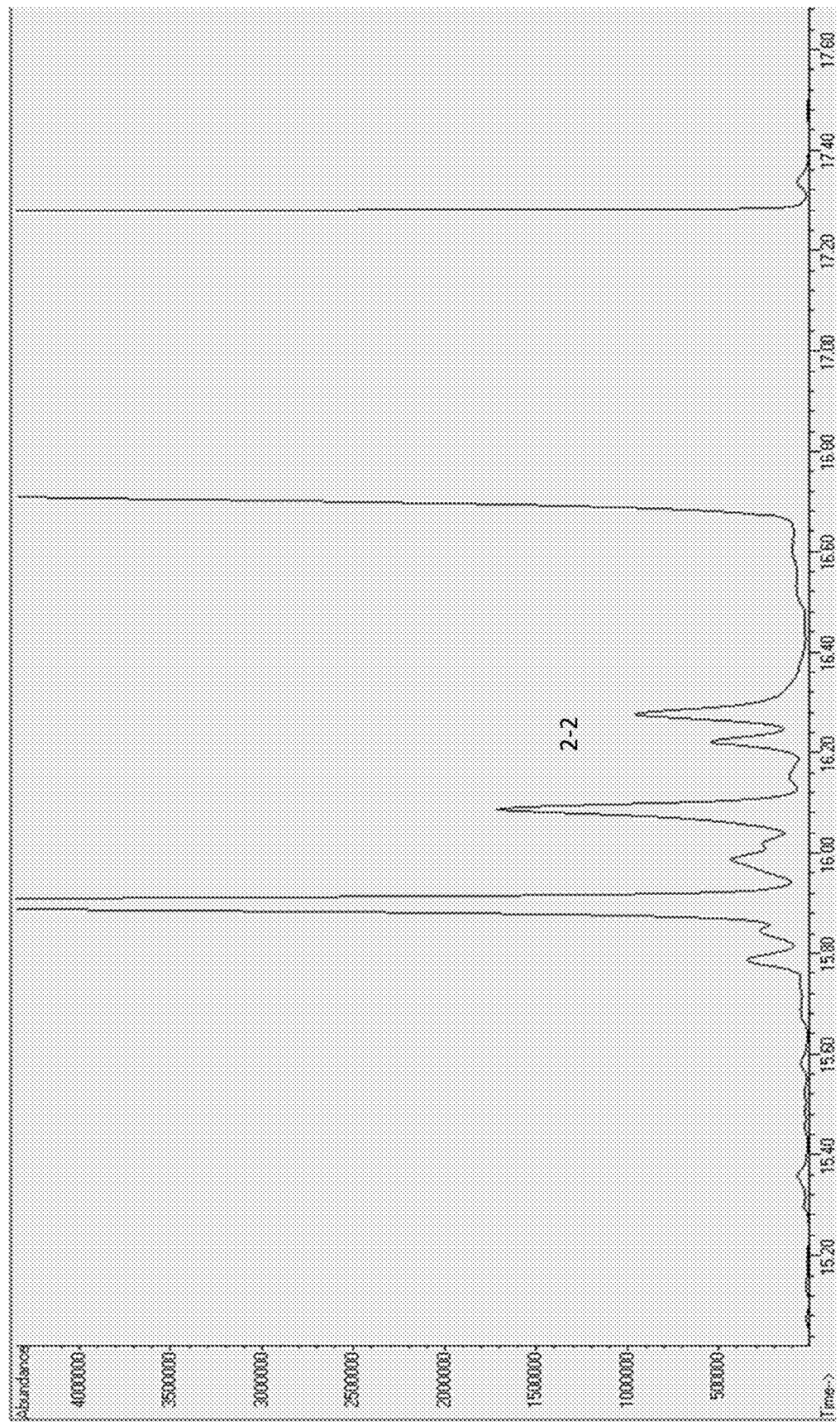

Further embodiments of the compositions are characterized in a GC/MS analysis, (exemplary spectra are shown in FIG. 2A and FIG. 2B), wherein the second component of the composition has a retention time from 15.0 minutes and 16.5 minutes, and a fragmentation pattern including one or more peaks at a mass-to-charge ratio (m/z) that includes 31, 41, 67, 79, 91, 93, 119, 149, 167, or a combination thereof, wherein the GC/MS analysis includes eluting the composition from a BP-1 capillary column of 60 meters in length, 320 µm in inner diameter and 1 µm in film thickness, with a liquid phase of 100% dimethylpolysiloxane and a carrier gas of helium, flown at 2 mL/min, under an inlet temperature of 250° C. and operated at a stepping temperature in a sequence of 50° C. for 2 minutes, then increasing temperature from 50° C. to 180° C. at an increment of 15° C./min, then increasing temperature from 180° C. to 250° C. at an increment of 30° C./min, followed by 250° C. for 6 minutes, and operated with an electron energy of 70 eV, an electron source temperature of 230° C., a quadrupole mass filter temperature of 150° C. and a scan for mass in a range between 20.0 m/z and 230.0 m/z with 0 minute's solvent delay.

One embodiment of the compositions provides, when characterized in the GC/MS analysis, the second component of the composition has a fragmentation pattern including peaks at m/z of 31, 41, 67, 79, 91, 93, and 119.

Another embodiment of the compositions provides, when characterized in the GC/MS analysis, the second component of the composition has a retention time from 15.8 minutes to 16.0 minutes with a fragmentation pattern including peaks at m/z of 149 and 167.

Yet another embodiment of the compositions provides, when characterized in the GC/MS analysis, the second component of the composition has a retention time from 15.8 minutes to 16.0 minutes with a fragmentation pattern further including one or more peaks at m/z selected from the group consisting of 31, 41, 67, 79, 91, 93 and 119.

A further embodiment of the compositions provides, when characterized in the GC/MS analysis, the second component of the composition has a retention time from 15.8 minutes to 16.0 minutes with a fragmentation pattern including peaks at m/z of at least 31, 41, 67, 79, 91, 93, 119, 149 and 167.

One embodiment of the compositions provides, when characterized in the GC/MS analysis, the second component of the composition has a retention time from 16.2 minutes to 16.4 minutes with a fragmentation pattern including peaks at m/z of 149 and 167.

Another embodiment of the compositions provides, when characterized in the GC/MS analysis, the second component of the composition has a retention time from 16.2 minutes to 16.4 minutes with a fragmentation pattern that further includes one or more peaks at m/z of 31, 41, 67, 79, 91, 93 and 119.

Yet another embodiment of the compositions provides, when characterized in the GC/MS analysis, the second component of the composition has a retention time from 16.2 minutes to 16.4 minutes with a fragmentation pattern including peaks at m/z of 31, 41, 67, 79, 91, 93, 119, 149, and 167.

Additional embodiments of the compositions provide, when characterized in the GC/MS analysis, the first component of the composition has a retention time from 16.5 minutes to 17.5 minutes, and in some embodiments with a fragmentation pattern including peaks at m/z of one or more of 31, 41, 67, 79, 91, 93, 119, 147, 165, and 178.

In one embodiment, the first component of the compositions in the GC/MS analysis has a fragmentation pattern including peaks at m/z of 31, 41, 67, 79, 91, 93 and 119.

In another embodiment, the first component of the compositions in the GC/MS analysis has a fragmentation pattern including peaks at m/z of 147, 165 and 178. In yet another embodiment, the first component of the composition in the GC/MS analysis has a fragmentation pattern including peaks at m/z of 31, 41, 67, 79, 91, 93, 119, 147, 165 and 178.

Further embodiments of the compositions, when characterized in the GC/MS analysis, have the third component eluted at a retention time of 14.0 minutes and 14.5 minutes. In further embodiments, the third component in the GC/MS analysis has a fragmentation pattern including a peak at m/z of 135.

The compositions of the present application include a first component which is TCDDM. In some embodiments of the compositions, the TCDDM has a chemical structure represented by formula (II):

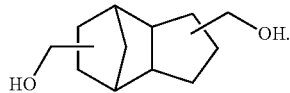

In some embodiments of the compositions, the TCDDM is selected from at least one of 3,8-bis(hydroxymethyl)tricyclo[$5.2.1.0^{2-6}$]decane; 3,9-bis(hydroxymethyl)tricyclo[$5.2.1.0^{2-6}$]decane; 4,8-bis(hydroxymethyl)tricyclo[$5.2.1.0^{2-6}$]decane; 4,9-bis(hydroxymethyl)tricyclo[$5.2.1.0^{2-6}$]decane; 5,8-bis(hydroxymethyl)tricyclo[$5.2.1.0^{2-6}$]decane; and 5,9-bis(hydroxymethyl)tricyclo[$5.2.1.0^{2-6}$]decane.

Some embodiments of the compositions provide the second component is an aliphatic diol. In one embodiment, the second component is a C12 (12-carbon, or $C_{12}$) aliphatic diol. In another embodiment, the second component is a C12 saturated cycloaliphatic diol. In further embodiments, the second component is one or a mixture of compounds represented by formula (XI):

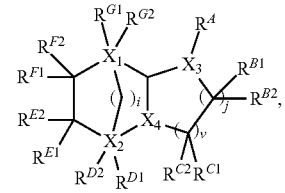

wherein (1) $X_1$ is C; (2) $X_2$ is C; (3) i=1 or 0; (4) j=1 or 0; (5) v=1 or 0; and (6) if i=1, then j=v=0, $R^{B1}$, $R^{B2}$, $R^{C1}$, $R^{C2}$, $R^{D1}$ and $R^{G1}$ are absent, ($X_3$—$R^4$) is a linear or branched $C_4$ (4-carbon) alkyl alcohol, $X_4$ is $CH_2$ or $CH(CH_2OH)$, and if $X_4$ is $CH_2$, then one of $R^{D2}$, $R^{E1}$, $R^{E2}$, $R^{F1}$, $R^{F2}$ and $R^{G2}$ is $CH_2OH$ whereas the other five of $R^{D2}$, $R^{E1}$, $RE^2$, $R^{F1}$, $R^{F2}$ and $R^{G2}$ are H; if $X_4$ is $CH(CH_2OH)$, then $R^{D2}$, $R^{E1}$, $R^{E2}$, $R^{F1}$, $R^{F2}$ and $R^{G2}$ are H; (7) if i=0, then j=v=1, $X_3$ is CH, $X_4$ is CH, one of $R^A$, $R^{B1}$, $R^{B2}$, $R^{C1}$ and $R^{C2}$ is $CH_2OH$ whereas the other four of $R^A$, $R^{B1}$, $R^{B2}$, $R^{C1}$ and $R^{C2}$ are H, one of $R^{D1}$, $R^{D2}$, $R^{E1}$, $R^{E2}$, $R^{F1}$, $R^{F2}$, $R^{G1}$ and $R^{G2}$ is $CH_2OH$, another one of $R^{D1}$, $R^{D2}$, $R^{E1}$, $R^{E2}$, $R^{F1}$, $R^{F2}$, $R^{G1}$ and $R^{G2}$ is $CH_3$, whereas the other six of $R^{D1}$, $R^{D2}$, $R^{E1}$, $R^{E2}$, $R^{F1}$, $R^{F2}$, $R^{G1}$ and $R^{G2}$ are H. Yet in a further embodiment, the second component of the compositions includes any one or more of

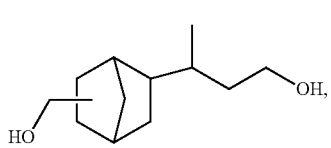

(XI)

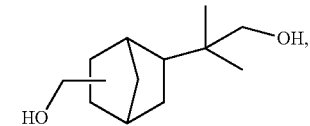

(XII)

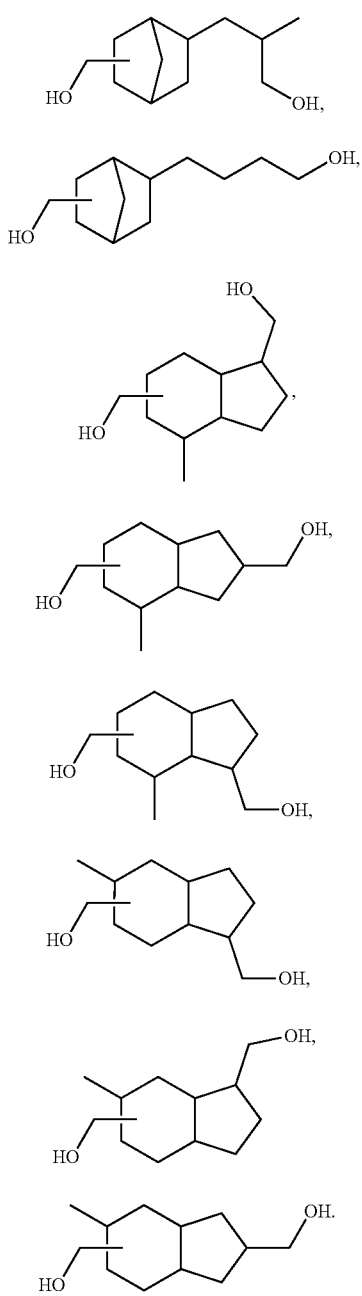

In any of formulae (XV)-(XX), one of the hydroxymethyl group may bond to the same carbon that a methyl group bonds to in the cycloalkane ring hence the second component of the composition can be:

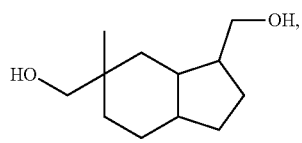

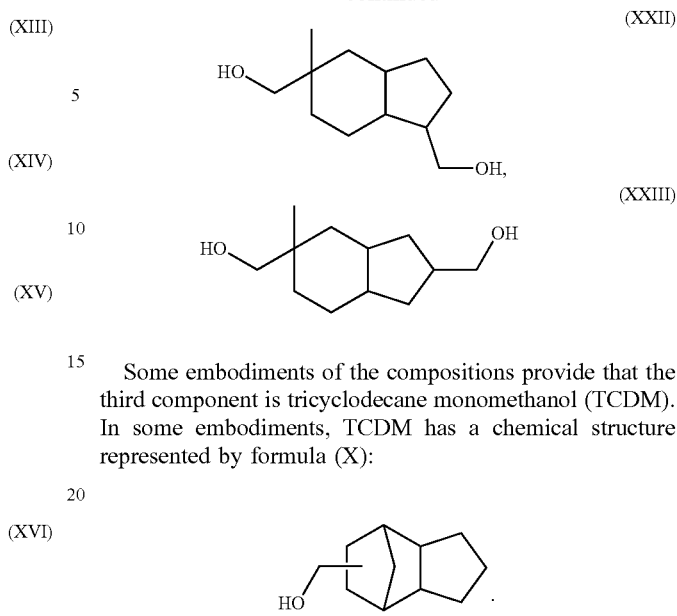

Some embodiments of the compositions provide that the third component is tricyclodecane monomethanol (TCDM). In some embodiments, TCDM has a chemical structure represented by formula (X):

In other embodiments, the third component of the compositions is a saturated C11 (11-carbon) cycloaliphatic compound with one hydroxyl group.

In further embodiments, the third component of the compositions is selected from at least one of 4-hydroxymethyltricyclo[5.2.1.0$^{2-6}$]decane, 3-hydroxymethyltricyclo[5.2.1.0$^{2-6}$]decane, and 5-hydroxymethyltricyclo[5.2.1.0$^{2-6}$]decane.

The compositions of the present application may have one or more components in addition to the first, the second and/or the third components described above, and the additional components do not adversely affect the property of the compositions for intended applications. Exemplary additional components include but are not limited to an acetal-containing compound; an amine-containing compound, such as tertiary amines (trimethylamine, triethylamine, tri-n-butylamine, tri-n-octylamine, triethanolamine, N-methyldiethanolamine and N,N-dimethylethanolamine), aromatic tertiary amines (N,N-dimethylaniline, N,N-diethylaniline and triphenylaniline), and heterocyclic tertiary amines (pyridine and quinoline); an alcohol-containing compound, such as ethylene glycol, 1,3-propanediol, 1,2-propanediol, 1,4-butanediol, 1,2-butanediol, 1,3-butanediol, 2,3-butanediol, 2-methyl-1,4-butanediol, 1,5-pentanediol, 2-methyl-1,3-propanediol, 2-methyl-1,3-pentanediol, 2-methyl-1,5-pentanediol, 3-methyl-1,5-pentanediol, 2,4-diethyl-1,5-pentanediol, neopentyl glycol, 1,6-hexanediol, 1,7-heptanediol, 1,8-octanediol, glycerol, pentaerythritol, 2-methyl-1,8-octanediol, 1,9-nonanediol, 1,10-decanediol, and trimethylolpropane; or an aldehyde-containing compound, such as tricyclodecane dicarbaldehyde and pentacyclopentadecane dicarbaldehyde.

The compositions of the present application may also include one or more additives. Exemplary additives do not adversely affect the compositions for intended applications and include, but are not limited to, stabilizers, antioxidants, lubricants, flame retardants, carbon black, coloring materials, defoaming agents, dispersing agents, viscosity modifiers, thixotropic agents, leveling agents, coupling agents, mold-release agents, anti-mildew agents, anti-bacterial agents, or the like.

Some embodiments provide the TCDDM-based compositions of the invention can be used as optical materials. In some embodiments, TCDDM-based compositions of the present application are added with polyester, epoxy, acrylate, polycarbonate, polycarbonate diol, and/or polyurethane resins or optical products therefrom. In some embodiments, TCDDM-based compositions of the present application are used to prepare polyester, epoxy, acrylate, polycarbonate, polycarbonate diol, and/or polyurethane, and the polymer containing the TCDDM residual is processed into an optical disc, a fiber, or a lens.

In some embodiments, polyesters can be prepared with the TCDDM-based compositions and a carboxylic acid-containing compound, such as a benzenedicarboxylic acid, a benzenetricarboxylic acid, or both, and optionally in further combination with an alkanediol. Exemplary benzenedicarboxylic acid includes a phthalic acid (1,2-benzenedicarboxylic acid), isophthalic acid (1,3-benzenedicarboxylic acid), or terephthalic acid (1,4-benzenedicarboxylic acid). Exemplary benzenetricarboxylic acid includes trimesic acid (benezene-1,3,5-tricarboxylic acid) or trimellitic acid (benzene-1,2,4-tricarboxylic acid). An alkanediol may be a $C_2$-$C_6$ linear or branched alkane with two hydroxyl groups.

In one embodiment, a polyester is derived from a TCDDM-based composition, terephthalic acid, trimellitic acid, and ethylene glycol. In CIELAB color space, scale b* indicates yellowing. Polyesters derived from the TCDDM-based compositions of the present application have improved resistance to yellowing.

The compositions of the present application can be prepared by one or more methods. For example, the composition is prepared by hydroformylation of dicyclopentadiene (DCPD), followed by phase separation and extraction, which is subsequently hydrogenated. In another embodiment, the hydrogenated product can be distilled by any known method, for example, the skilled artisan can adjust the distillation column height or theoretical stages. In yet another embodiment, the skilled artisan can adjust the reflux ratio or distillation pressure, or add metal compound in a distillation process. The various preparation processes provided above do not infer that the compositions of the present application can only be prepared in these processes.

Exemplary processes in making the compositions of the present application are provided below.

Various embodiments provide the disclosed compositions of the present application are made by a hydrogenation process of tricyclodecane dialdehyde. Further embodiments provide a disclosed composition is made by a hydrogenation process of a tricyclodecane dialdehyde that is obtained from or as a component within an aqueous extraction layer of the hydroformylation product of dicyclopentadiene. In some embodiments, the hydrogenation process includes introducing hydrogen gas at an increased pressure, such as between about 2 MPa and 10 MPa, to the tricyledecane dialdehyde or to the hydroformylation product of dicyclopentadiene, and the hydroformylation product of dicyclopentadiene includes at least tricyclodecane dialdehyde. In further embodiments, the hydrogenation process is conducted at a temperature in a range between 40° C. and 200° C., or between about 60° C. and 150° C. In yet another embodiment, the hydrogenation process takes place in the presence of, or by adding to the reactant, a catalyst such as nickel, aluminum, or a combination thereof. Further processes of hydrogenation are disclosed in U.S. Pat. No. 6,365,782, the content of which is incorporated herein by reference.

The disclosure is further illustrated by the following examples which should not be construed as limiting. The examples are illustrative only and are not intended to limit any of the embodiments described herein. The following examples do not in any way limit the invention.

EXAMPLES

The following examples are not intended to limit the scope of the claims to the invention, but are rather intended to be exemplary of certain embodiments. Any variations in the exemplified processes which occur to the skilled artisan are intended to fall within the scope of the invention.

The present application will be further explained by the following examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

TCDDM-Based Compositions

Preparation Example

Hydroformylation to obtain the aldehyde compound as a pre-cursor of the TCDDM-based composition was performed under an atmosphere of hydrogen and carbon monoxide at 1:1 ratio. Specifically, 100 g methylcyclohexane, 0.015 g Rh(acac)(CO)$_2$ (Aldrich), and 4.5 g tris-(2,4-di-t-butylphenyl)phosphite (BASF) were mixed together to form a hydroformylation mixture. The hydroformylation mixture was heated to 70° C. for 1.5 hours to dissolve evenly. Once this procedure was completed, the hydroformylation mixture was poured into an autoclave at a pressure of 1 kg/cm$^2$G. After that, the temperature and pressure of the autoclave are increased to 80° C. and 50 kg/cm$^2$G, respectively. 50 g dicyclopentadiene (DCPD) (Zeon) was continuously fed into the autoclave at a rate of 0.83 g/min over a period of 30 minutes using a duplex pump. The reaction was allowed to proceed for 12 hours at a pressure of 50 kg/cm$^2$G. After the reaction was complete, a non-aqueous hydroformylation product solution was obtained.

Example 1

The non-aqueous hydroformylation product solution (174.5 g) obtained from the preparation example and an aqueous extraction solvent containing 2-methyl-1,3-propanediol (MPO), methanol and water at a weight ratio of 1:7:2 (MPO:methanol:water) were mixed at the mass ratio of 1:1 (non-aqueous hydroformylation product solution: aqueous extraction solvent), and stirred in a mixer which was held at a temperature of 25° C. After 1 hour stirring, the mixture was poured into a glass extractor and stood for 2 hours and a biphasic mixture (non-aqueous hydroformylation solvent layer (i.e., nonpolar phase) and aqueous extraction solvent layer (i.e., polar phase)) was obtained. The extraction temperature was held at 25° C. Subsequently, 0.5 g of Nickel/Al$_2$O$_3$ was added into 100 g of the aqueous extraction layer, and a hydrogen gas pressure of 5 MPa was introduced to proceed with the hydrogenation process in a temperature of 60° C. for about 3 hours. After that, the hydrogenation product (253.1 g) was distilled on a Claisen head with condenser at a pressure of 12 hPa and the TCDDM-based composition (57.1 g) in a boiling range of 170° C.-210° C. was obtained.

Example 2

The non-aqueous hydroformylation product solution (174.5 g) obtained from the preparation example and an aqueous extraction solvent containing tricyclo[5.2.1.0(2,6)]decanedimethanol, methanol and water at a weight ratio of 1:7:2 (tricyclo[5.2.1.0(2,6)]decanedimethanol:methanol:water) were mixed at the mass ratio of 1:1 (non-aqueous hydroformylation product solution:aqueous extraction solvent), and stirred in a mixer which was held at a temperature of 35° C. After 1 hour stirring, the mixture was poured into a glass extractor and stood for 2 hours and a biphasic mixture was obtained. The extraction temperature was held at 35° C. Subsequently, 0.5 g of Nickel/$Al_2O_3$ was added into 100 g of the aqueous extraction layer, and a hydrogen gas pressure of 8 MPa was introduced to proceed with the hydrogenation process in a temperature of 80° C. for about 3 hours. After that, the hydrogenation product (252.4 g) was distilled on a Claisen head with condenser at a pressure of 10 hPa and the TCDDM-based composition (75.1 g) in a boiling range of 170° C.-210° C. was obtained.

Example 3

The non-aqueous hydroformylation product solution (174.5 g) obtained from the preparation example and an aqueous extraction solvent containing MPO, methanol and water at a weight ratio of 7:1:2 (MPO:methanol:water) were mixed at the mass ratio of 1:1 (non-aqueous hydroformylation product solution:aqueous extraction solvent) and stirred in a mixer which was held at a temperature of 70° C. After 1 hour stirring, the mixture was poured into a glass extractor and stood for 2 hours and a biphasic mixture was obtained. The extraction temperature was held at 70° C. Subsequently, 0.5 g of Nickel/$Al_2O_3$ was added into 100 g of the aqueous extraction layer, and a hydrogen gas pressure of 2 MPa was introduced to proceed with the hydrogenation process in a temperature of 150° C. for about 3 hours. After the hydrogenation process, pressure was released and the reaction was cooled to room temperature. After that, the hydrogenation product (264.7 g) was distilled on a Claisen head with condenser at a pressure of 5 hPa and the TCDDM-based composition (60.35 g) in a boiling range of 170° C.-210° C. was obtained.

Example 4

The non-aqueous hydroformylation product solution (174.5 g) obtained from the preparation example and an aqueous extraction solvent containing cyclohexanedimethanol (CHDM), methanol and water at a weight ratio of 1:6:3 (CHDM:methanol:water) were mixed at the mass ratio of 1:1 (non-aqueous hydroformylation product solution:aqueous extraction solvent) and stirred in a mixer which was held at a temperature of 30° C. After 1 hour stirring, the mixture was poured into a glass extractor and stood for 2 hours and a biphasic mixture was obtained. The extraction temperature was held at 30° C. Subsequently, 0.5 g of Nickel/$Al_2O_3$ was added into 100 g of the aqueous extraction layer, and a hydrogen gas pressure of 4 MPa was introduced to proceed with the hydrogenation process in a temperature of 80° C. for about 3 hours. After the hydrogenation process, pressure was released and the reaction was cooled to room temperature. After that, the hydrogenation product (258.7 g) was distilled on a Claisen head with condenser at a pressure of 4 hPa and the TCDDM-based composition (60.23 g) in a boiling range of 170° C.-210° C. was obtained.

Example 5

The non-aqueous hydroformylation product solution (174.5 g) obtained from the preparation example and an aqueous extraction solvent containing MPO, methanol and water at a weight ratio of 3:5:2 (MPO:methanol:water) were mixed at the mass ratio of 1:1 (non-aqueous hydroformylation product solution:aqueous extraction solvent) and stirred in a mixer which was held at a temperature of 20° C. After 1 hour stirring, the mixture was poured into a glass extractor and stood for 2 hours and a biphasic mixture was obtained. The extraction temperature was held at 20° C. Subsequently, 0.5 g of Nickel/$Al_2O_3$ was added into 100 g of the aqueous extraction layer, and a hydrogen gas pressure of 9 MPa was introduced to proceed with the hydrogenation process in a temperature of 100° C. for about 3 hours. After the hydrogenation process, pressure was released and the reaction was cooled to room temperature. After that, the hydrogenation product (257.9 g) was distilled on a Claisen head with condenser at a pressure of 4 hPa and the TCDDM-based composition (59.42 g) in a boiling range of 170° C.-210° C. was obtained.

Example 6

The non-aqueous hydroformylation product solution (174.5 g) obtained from the preparation example and an aqueous extraction solvent containing MPO, ethanol (EtOH) and water at a weight ratio of 1:6:3 (MPO:EtOH:water) were mixed at the mass ratio of 1:1 (non-aqueous hydroformylation product solution:aqueous extraction solvent) and stirred in a mixer which was held at a temperature of 40° C. After 1 hour stirring, the mixture was poured into a glass extractor and stood for 2 hours and a biphasic mixture was obtained. The extraction temperature was held at 40° C. Subsequently, 0.5 g of Nickel/$Al_2O_3$ was added into 100 g of the aqueous extraction layer, and a hydrogen gas pressure of 4 MPa was introduced to proceed with the hydrogenation process in a temperature of 120° C. for about 3 hours. After the hydrogenation process, pressure was released and the reaction was cooled to room temperature. After that, the hydrogenation product (264.2 g) was distilled on a Claisen head with condenser at a pressure of 8 hPa and the TCDDM-based composition (58.42 g) in a boiling range of 170° C.-210° C. was obtained.

Example 7

The non-aqueous hydroformylation product solution (174.5 g) obtained from the preparation example and an aqueous extraction solvent containing tricyclo[5.2.1.0(2,6)]decanedimethanol, methanol and water at a weight ratio of 1:6:3 (tricyclo[5.2.1.0(2,6)]decanedimethanol:methanol:water) were mixed at the mass ratio of 1:1 (non-aqueous hydroformylation product solution:aqueous extraction solvent) and stirred in a mixer which was held at a temperature of 55° C. After 1 hour stirring, the mixture was poured into a glass extractor and stood for 2 hours and a biphasic mixture was obtained. The extraction temperature was held at 55° C. Subsequently, 0.5 g of Nickel/$Al_2O_3$ was added into 100 g of the aqueous extraction layer, and a hydrogen gas pressure of 7 MPa was introduced to proceed with the hydrogenation process in a temperature of 85° C., for about 3 hours. After the hydrogenation process, pressure was released and the reaction was cooled to room temperature. After that, the hydrogenation product (254.1 g) was distilled on a Claisen head with condenser at a pressure of 6 hPa and the TCDDM-based composition (75.5 g) in a boiling range of 170° C.-210° C. was obtained.

Example 8

The non-aqueous hydroformylation product solution (174.5 g) obtained from the preparation example and an aqueous extraction solvent containing MPO, methanol and water at a weight ratio of 8:1.5:0.5 (MPO:methanol:water) were mixed at the mass ratio of 1:1 (non-aqueous hydroformylation product solution:aqueous extraction solvent) and stirred in a mixer which was held at a temperature of 30° C. After 1 hour stirring, the mixture was poured into a glass extractor and stood for 2 hours and a biphasic mixture was obtained. The extraction temperature was held at 30° C. Subsequently, 0.5 g of Nickel/$Al_2O_3$ was added into 100 g of the aqueous extraction layer, and a hydrogen gas pressure of 10 MPa was introduced to proceed with the hydrogenation process in a temperature of 65° C. for about 3 hours. After the hydrogenation process, pressure was released and the reaction was cooled to room temperature. After that, the hydrogenation product (262.3 g) was distilled on a Claisen head with condenser at a pressure of 11 hPa and the TCDDM-based composition (56.7 g) in a boiling range of 170° C.-210° C. was obtained.

Example 9

The non-aqueous hydroformylation product solution (174.5 g) and an aqueous extraction solvent containing MPO and water at a weight ratio of 8:2 were mixed at the mass ratio of 1:1 (non-aqueous hydroformylation product solution:aqueous extraction solvent) and stirred in a mixer which was held at a temperature of 40° C. After 1 hour stirring, the mixture was poured into a glass extractor and stood for 2 hours and a biphasic mixture was obtained. The extraction temperature was held at 40° C. Subsequently, 0.5 g of Nickel/$Al_2O_3$ was added into 100 g of the aqueous extraction layer, and a hydrogen gas pressure of 3 MPa was introduced to proceed with the hydrogenation process in a temperature of 140° C., for about 3 hours. After the hydrogenation process, pressure was released and the reaction was cooled to room temperature. After that, the hydrogenation product (256.6 g) is distilled on a Claisen head with condenser at a pressure of 4 hPa and the TCDDM-based composition (59.2 g) in a boiling range of 170° C.-210° C. was obtained.

Comparative Example 1

The non-aqueous hydroformylation product solution (174.5 g) obtained from the preparation example and an aqueous extraction solvent containing propylene glycol and water at a weight ratio of 8:2 (propylene glycol:water) were mixed at the mass ratio of 1:1 (non-aqueous hydroformylation product solution:aqueous extraction solvent) and stirred in a mixer which was held at a temperature of 35° C. After 1 hour stirring, the mixture was poured into a glass extractor and stood for 2 hours and a biphasic mixture was obtained. The extraction temperature was held at 35° C. Subsequently, 0.5 g of Nickel/$Al_2O_3$ was added into 100 g of the aqueous extraction layer, and a hydrogen gas pressure of 2 MPa was introduced to proceed with the hydrogenation process in a temperature of 60° C., for about 3 hours. After the hydrogenation process, pressure was released and the reaction was cooled to room temperature. After that, the hydrogenation product (245.4 g) is distilled on a Claisen head with condenser at a pressure of 4 hPa and the TCDDM-based composition (57.1 g) in a boiling range of 170° C.-210° C. was obtained (("Comparative Example 1").

Comparative Example 2

The non-aqueous hydroformylation product solution (174.5 g) obtained from the preparation example and an aqueous extraction solvent containing methanol and water at a weight ratio of 8:2 (methanol:water) were mixed at the mass ratio of 1:1 (non-aqueous hydroformylation product solution:aqueous extraction solvent) and stirred in a mixer which was held at a temperature of 25° C. After 1 hour stirring, the mixture was poured into a glass extractor and stood for 2 hours and a biphasic mixture was obtained. The extraction temperature was held at 25° C. Subsequently, 0.5 g of Nickel/$Al_2O_3$ was added into 100 g of the aqueous extraction layer, and a hydrogen gas pressure of 6 MPa was introduced to proceed with the hydrogenation process in a temperature of 70° C., for about 3 hours. After the hydrogenation process, pressure was released and the reaction was cooled to room temperature. After that, the hydrogenation product (236.8 g) is distilled on a Claisen head with condenser at a pressure of 10 hPa and the TCDDM-based composition (48.4 g) in a boiling range of 170° C.-210° C. was obtained ("Comparative Example 2").

Comparative Example 3

The non-aqueous hydroformylation product solution (174.5 g) obtained from the preparation example and an aqueous extraction solvent of propylene glycol were mixed at the mass ratio of 1:1 (non-aqueous hydroformylation product solution:propylene glycol) and stirred in a mixer which was held at a temperature of 30° C. After 1 hour stirring, the mixture was poured into a glass extractor and stood for 2 hours and a biphasic mixture was obtained. The extraction temperature was held at 30° C. Subsequently, 0.5 g of Nickel/$Al_2O_3$ was added into 100 g of the aqueous extraction layer, and a hydrogen gas pressure of 4 MPa was introduced to proceed with the hydrogenation process in a temperature of 100° C., for about 3 hours. After the hydrogenation process, pressure was released and the reaction was cooled to room temperature. After that, the hydrogenation product (220.0 g) is distilled on a Claisen head with condenser at a pressure of 3 hPa and the TCDDM-based composition (41.8 g) in a boiling range of 170° C.-210° C. was obtained ("Comparative Example 3").

Gas Chromatography (GC) Analysis

The TCDDM-based compositions were analyzed in gas chromatography (GC). GC was carried out using Agilent 6890 system, including a BP-5 column (manufactured by SGE Analytical Science) 30 m×530 μm×1 μm (length×inner diameter×film thickness), with a liquid phase of 5% phenyl 95% dimethylpolysiloxane, a carrier gas of nitrogen, at a flow velocity of the following sequence: 5 mL/min for the first 11 minutes, followed by a stepping velocity which increases from 5 mL/min to 10 mL/min at an increment of 1 mL/min, and subsequently maintained at 10 mL/min till the end of GC. The sample inlet temperature was 250° C.; the flame ionization detector temperature was 300° C.; sample injection volume was 2 μL, and the temperature followed this sequence: 50° C. for the first minute, followed by a stepping temperature which increased from 50° C. to 180° C. at an increment of 15° C./min and then increased from 180° C. to 250° C. at an increment of 30° C./min, and subsequently maintained at 250° C. for eight minutes.

The detailed parameters for GC analysis are shown in Table 1 for reference.

TABLE 1

| Oven | Initial temp: 50 ° C. (On) | Maximum temp: 300 ° C. |
| --- | --- | --- |
| | Initial time: 1.00 min | Equilibration time: 0.20 min |

| Ramps: | | | |
| --- | --- | --- | --- |
| # | Rate | Final temp | Final time |
| 1 | 15.00 | 180 | 0.00 |
| 2 | 30.00 | 250 | 8.00 |
| 3 | 0.0 (off) | | |

Post temp: 50° C.
Post time: 0.00 min
Runtime: 20.00 min

| INLET (SPLIT/SPLITLESS) | Mode: Split | Initial temp: 250 ° C. (On) |
| --- | --- | --- |
| | Pressure: 3.46 psi (On) | Split ratio: 10:1 |
| | Split flow: 50.0 mL/min | Total flow: 57.2 mL/min |
| | Gas saver: On | Saver flow: 20.0 mL/min |
| | Saver time: 2.00 min | Gas type: Nitrogen |
| COLUMN | Capillary Column | |
| | Model Number: SGE | BP-5 (5% phenyl; 95% dimethyl-polysiloxane) |
| | | Nominal length: 30.0 m |
| | Max temperature: 300 ° C. | Nominal film thickness: 1 μm |
| | Nominal diameter: 530.00 μm | |
| | Mode: ramped flow | |
| | Initial flow: 5.0 mL/min | Initial time: 11.00 min |

| # | Rate | Final flow | Final time |
| --- | --- | --- | --- |
| 1 | 1.00 | 10.0 | 0.00 |
| 2 | 0.0 (Off) | | |

Post flow: 0.0 mL/min
Average velocity: 37 cm/sec
Outlet: Detector
Outlet pressure: ambient Nominal init pressure: 3.47 psi

| DETECTOR (FID) | Temperature: 300 ° C. (On) | Hydrogen flow: 40.0 mL/min (On) |
| --- | --- | --- |
| | Air flow: 450.0 mL/min (On) | Mode: Constant makeup flow |
| | Makeup flow: 20.0 mL/min (On) | Makeup Gas Type: Nitrogen |
| | Flame: On | Electrometer: On |
| | Lit offset: 2.0 | |
| SIGNAL | Data rate: 5 Hz | Type: detector |
| | Save Data: On | Zero: 0.0 (Off) |
| | Range: 0 | Fast Peaks: Off |
| | Attenuation: 0 | |
| COLUMN COMP | Derive from detector | |
| POST RUN | Post Time: 0.00 min | |

FIG. 1 shows the GC retention time spectrum of the TCDDM-based composition of Example 4, where bracket 1 refers to the peaks at a retention time between 12.4 minutes and 13 minutes ("Peak 1") indicating a first component in the composition, bracket 2 refers the peaks at a retention time between 11.8 minutes and 12.4 minutes ("Peak 2") indicating a second component in the composition, and peaks labeled "3" refer to the peaks at a retention time of around 10.8 minutes to 11.2 minutes ("Peak 3") indicating a third component in the composition.

Figure 3:
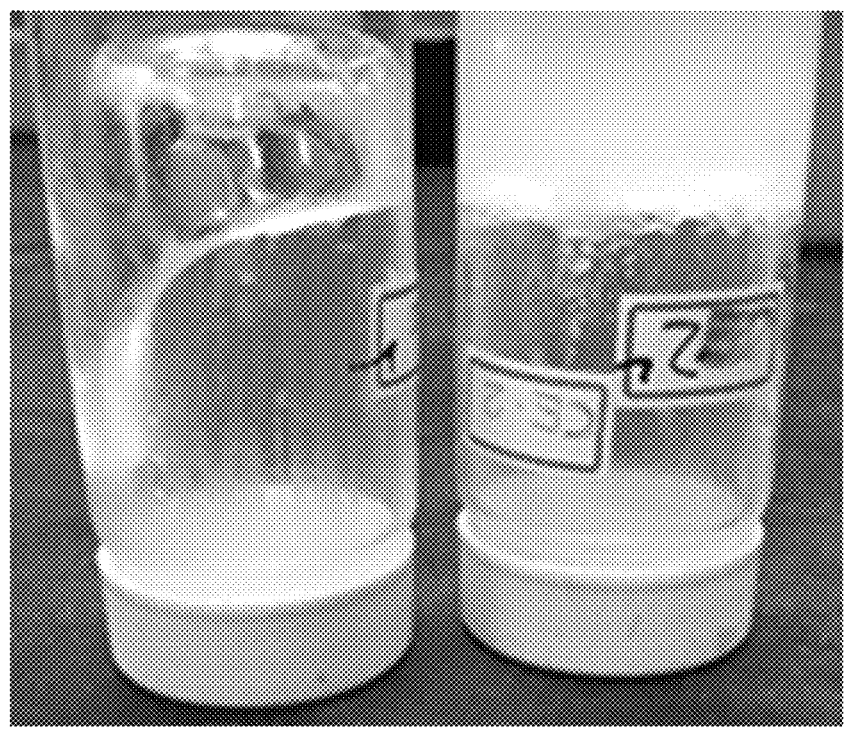
FIG. 3 is a photograph of the TCDDM-based composition of Example 6 (in the inverted bottle on the left) and that of Comparative Example 2 (in the inverted bottle on the right).

Further analysis of the GC spectra revealed differences in at least the amount of the second component between the Examples and the Comparative Examples. Tables 2 and 3 summarize the relative area under curve of Peak 1 (annotated as "1"), Peak 2 (annotated as "2") and Peak 3 (annotated as "3"), and "total" is the sum of area under all curves during the measurement time (excluding solvent). Examples 1-9 were different from the Comparative Examples 1-3 at least with respect to the area under curve of Peak 2 relative to the area under curve of Peak 1, denoted "Peak 2/Peak 1 value". Specifically, Examples 1-9 have Peak 2/Peak 1 value in a range between 0.001 and 0.04, whereas the Peak 2/Peak 1 value of Comparative Examples 1-3 is outside of this range. As shown in FIG. 3, Comparative Example 2 (right bottle) whose Peak 2/Peak 1 value was 0.000801, was more solid-like and rigid than Example 6 (left bottle), (did not pass in terms of fluidity, wherein the fluidity is determined by turning the bottles upside down and waiting for two minutes to see whether the compositions are flowable), thereby not amenable to further mixing or other processing.

TABLE 2

| GC result | Example 1 | Example 2 | Example 3 | Example 4 | Example 5 | Example 6 | Example 7 | Example 8 | Example 9 |
|---|---|---|---|---|---|---|---|---|---|
| Peak 1/total | 0.9895 | 0.9934 | 0.9878 | 0.9618 | 0.9723 | 0.9902 | 0.9937 | 0.9975 | 0.9913 |
| Peak 2/total | 0.00946 | 0.00642 | 0.01122 | 0.0371 | 0.02704 | 0.0076 | 0.0062 | 0.0012 | 0.00353 |
| Peak 3/total | 0.00034 | 0.00015 | 0.00034 | 0.0011 | 0.00032 | 0.0018 | 0.0001 | 0.00032 | 0.00465 |
| Peak 2/Peak 1 | 0.00956 | 0.006463 | 0.011359 | 0.038574 | 0.02781 | 0.007675 | 0.006239 | 0.001203 | 0.003561 |
| Peak 3/Peak 1 | 0.000344 | 0.000151 | 0.000344 | 0.001144 | 0.000329 | 0.001818 | 0.000101 | 0.000321 | 0.004691 |
| fluidity | pass | pass | pass | pass | pass | pass | pass | pass | pass |

TABLE 3

| GC result | Comparative Example 1 | Comparative Example 2 | Comparative Example 3 |
|---|---|---|---|
| Peak 1/total | 0.9554 | 0.999 | 0.9436 |
| Peak 2/total | 0.044 | 0.0008 | 0.0461 |
| Peak 3/total | 0.0006 | 0.0001 | 0.00734 |
| Peak 2/Peak 1 | 0.046054 | 0.000801 | 0.04886 |
| Peak 3/Peak 1 | 0.000628 | 0.0001 | 0.00778 |
| fluidity | pass | failed | pass |

Gas Chromatography/Mass Spectrometry Analysis

The TCDDM-based compositions were further analyzed in gas chromatography/mass spectrometry (GC/MS). GC/MS was carried out with Agilent 6890 GC system and Agilent 5975 inert MSD (G3171A). The GC portion included BP-1 column (manufactured by SGE Analytical Science) 60 m×320 μm×1 μm (length×inner diameter×film thickness), a liquid phase of 100% dimethylpolysiloxane, a carrier gas of helium flown at 2 mL/min. The sample inlet temperature was 250° C., and the temperature increase condition was as followed: 50° C. for the initial two minutes, followed by a stepping temperature which increased from 50° C. to 180° C. at an increment of 15° C./min and then increased from 180° C. to 250° C. at an increment of 30° C./min, and subsequently maintained at 250° C. for 6 minutes. Then the MS analysis began. The MS portion was operated with an electron ionization energy of 70 eV, source temperature of 230° C., quadrupole mass filter temperature of 150° C. and a scan range from 20 m/z to 230 m/z.

The detailed parameters for GC/Mass analysis are shown in Table 4 for reference.

TABLE 4

| | | |
|---|---|---|
| Oven | Initial temp: 50° C. (On) | Maximum temp: 280° C. |
| | Initial time: 2.00 min | Equilibration time: 0.25 min |
| | Ramps: | |
| | # Rate Final temp Final time | |
| | 1  15.00  180  0.00 | |
| | 2  30.00  250  6.00 | |
| | 3  0.0 (off) | |
| | Post temp: 50° C. | |
| | Post time: 0.00 min | |
| | Runtime: 19.00 min | |
| INLET (SPLIT/SPLITLESS) | Mode: Split | Initial temp: 250° C. (On) |
| | Pressure: 12.81 psi (On) | Split ratio: 20:1 |
| | Split flow: 40.0 mL/min | Total flow: 44.9 mL/min |
| | Gas saver: On | Saver flow: 20.0 mL/min |
| | Saver time: 2.00 min | Gas type: Helium |
| COLUMN | Capillary Column | |
| | Model Number: SGE | BP-1 100% Dimethyl-polysiloxane |
| | Max temperature: 325° C. | Nominal length: 60.0 m |
| | Nominal diameter: 320.00 um | Nominal film thickness: 1.00 um |
| | Mode: constant flow | Initial flow: 2.0 mL/min |
| | Nominal init pressure: 12.82 psi | Average velocity: 36 cm/sec |
| | Outlet: MSD | |
| | Outlet pressure: vacuum | |
| THERMAL AUX | Use: MSD Transfer Line Heater | |
| | Description: | |
| | Initial temp: 280° C. (On) | |
| | Initial time: 0.00 min | |
| | # Rate Final temp Final time | |
| | 1  0.0 (Off) | |
| POST RUN | Post Time: 0.00 min | |
| MS ACQUISITION | General Information | |
| PARAMETERS | MS Information | |
| | Solvent Delay: 0.00 min | EM Absolute: True |
| | Resulting EM Voltage: 1800.0 | |
| | Scan Parameters | |

TABLE 4-continued

| | Low Mass: 20.0<br>Threshold: 150<br>MSZones<br>MS Quad: 150° C.<br>MS Source: 230° C. | High Mass: 230.0<br><br><br>Maximum: 200° C.<br>Maximum: 250° C. |
|---|---|---|
| TUNE<br>PARAMETERS | EMISSION: 34.610<br>REPELLER: 34.814<br>ENTRANCE_LE: 9.500<br>AMUGAIN: 1779.000<br>FILAMENT: 1.000<br>ENTLENSOFFS: 18.573<br>MASSOFFSET: −38.000 | ENERGY: 69.922<br>IONFOCUS: 90.157<br>EMVOLTS: 1858.824<br>AMUOFFSET: 119.813<br>DCPOLARITY: 0.000<br>MASSGAIN: −625.000 |

FIG. 2A shows a retention time spectrum in the GC/MS analysis of the TCDDM-based composition of Example 4, where bracket 1' refers to a retention time range between 16.5 minutes and 17.5 minutes ("Peak 1'") indicating a first component in the composition, bracket 2' refers to a retention time range between 15.0 minutes and 16.5 minutes ("Peak 2'") indicating a second component in the composition, and peaks labeled "3'" refers to a retention time range from 14.0 minutes to 14.5 minutes ("Peak 3'") indicating a third component in the composition.

FIG. 2B shows a detailed portion of the spectrum in bracket 2' in FIG. 2A, wherein the peaks at a retention time of around 15.8 minutes to 16.0 minutes were labeled "2-1" ("Peak 2-1") and the peaks at a retention time of around 16.2 minutes to 16.4 minutes were labeled "2-2" ("Peak 2-2").

The m/z related to the Peak 1', Peak 2', Peak 2-1, Peak 2-2, and Peak 3' were shown in Table 5.

TABLE 5

| | m/z |
|---|---|
| Peak 1' | 31, 41, 67, 79, 91, 93, 119, 147, 165, 178 |
| Peak 2' | 31, 41, 67, 79, 91, 93, 119 |
| Peak 2-1 | 31, 41, 67, 79, 91, 93, 119, 149, 167 |
| Peak 2-2 | 31, 41, 67, 79, 91, 93, 119, 149, 167 |
| Peak 3' | 31, 41, 67, 79, 91, 135 |

Polyester Derived from the TCDDM-Based Composition.

The TCDDM-based compositions of Examples 1-9 and Comparative Examples 1 and 3 was used to prepare the polyester of Examples 10-18 and Comparative Examples 4-5, respectively. Specifically, trimellitic acid (TMA) (Tokyo chemical industry Co.), the TCDDM-based compositions of each of Examples 1-9 and Comparative Examples 1 and 3, ethylene glycol (EG) (Oriental Union Chemical Corporation), and purified terephthalic acid (PTA) (China American Petrochemical Co.) were mixed in the autoclave with a molar ratio of 0.5:40:20:50. After that, 100 ppm titanium butoxide was added and mixed evenly under a stirring speed of 150 rpm at room temperature. The esterification proceeded in the condition of 4 atm and 220° C. After the amount of water produced by esterification reached 90% of theoretical value, the temperature was raised to 250° C. and the mixture was put under vacuum for 30 minutes. Subsequently, the temperature was raised to 280° C. for polycondensation. When the inherent viscosity of the composition reached about 0.6 to 0.7 dL/g, each mixture was cooled to room temperature and the polyester was collected.

The polyesters derived from each of the TCDDM-based compositions were further analyzed for color determination.

Inherent viscosity was determined according to ASTM D4603 standard. Briefly, about 0.25 g of polyester was weighed in a flask and dissolved with about 25 mL of solvents (phenol: 1,1,2,2-tetrachloroethane=60:40 (wt %)), and the solution was cooled to about room temperature. The solution was then poured into a clean and dry CANNON-Ubbelohde viscometer by passing it through a funnel and filtered into the top of the larger viscometer tube. The flow time was then recorded. The measurement was repeated for a total of at least three times, and the results are averaged. Inherent viscosity was determined as follows:

$$\eta_{inh} \frac{30° \text{C.}}{0.5\%} = \frac{\ln \eta_r}{C},$$

where $\eta_{inh}$ (unit is dl/g) is inherent viscosity at 30° C., $\eta_r$ is relative viscosity=$t/t_0$, where t refers average solution flow time in seconds and to refers to average solvent flow time in seconds, and C is polymer solution concentration (g/dL).

Color of polyester pellets was determined according to the ASTM D6290 standard and using NIPPON Denshoku NE 4000 color meter with a light source of D65/10 (standard illuminant D65) and presented as CIELAB color space (defined by the International Commission on Illumination) L*, a* and b*.

Tables 6 and 7 summarize the CIELAB color space of polyesters derived from the TCDDM-based compositions of Examples 1-9 and Comparative Examples 1 and 3 in combination with EG, PTA and TMA. In CIELAB color space, scale b* indicates yellowing. Polyesters derived from the TCDDM-based compositions of Examples 1-9, compared to those derived from Comparative Examples, have improved resistance to yellowing. Thus, it is believed that the TCDDM-based compositions present application claimed are suitable as raw materials for manufacturing downstream products with improved optical properties.

TABLE 6

| Polyester | TCDDM-based<br>composition source | L* | a* | b* |
|---|---|---|---|---|
| Example 10 | Example 1 | 64.25 | −0.9 | 4.73 |
| Example 11 | Example 2 | 64.91 | −0.61 | 3.95 |
| Example 12 | Example 3 | 64.77 | −0.14 | 5.43 |
| Example 13 | Example 4 | 70.06 | −0.13 | 7.49 |
| Example 14 | Example 5 | 62.63 | 0.37 | 6.73 |
| Example 15 | Example 6 | 66.35 | −0.26 | 6.48 |
| Example 16 | Example 7 | 65.33 | −0.22 | 4.05 |
| Example 17 | Example 8 | 68.38 | −0.89 | 5.48 |
| Example 18 | Example 9 | 62.41 | 1.02 | 6.12 |

TABLE 7

| Polyester | TCDDM-based composition source | L* | a* | b* |
|---|---|---|---|---|
| Comparative Example 4 | Comparative Example 1 | 63.65 | 0.11 | 8.64 |
| Comparative Example 5 | Comparative Example 3 | 65.94 | −0.53 | 10.34 |

The various processes and techniques described above provide a number of ways to carry out the application. Of course, it is to be understood that not necessarily all objectives or advantages described can be achieved in accordance with any particular embodiment described herein. Thus, for example, those skilled in the art will recognize that the processes can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform processes in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents and other publications identified in the specification and examples are expressly incorporated herein by reference for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail. These patents and other publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Various embodiments of the present application are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the present application known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the present application and its practical application and to enable others skilled in the art to utilize the present application in various embodiments and with various modifications as are suited to the particular use contemplated. Therefore, it is intended that the invention not be limited to the particular embodiments disclosed for carrying out the invention.

Although particular embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A composition comprising:
   a first component which is tricyclodecane dimethanol, and
   a second component,
   wherein when the composition is characterized in a gas chromatography, the tricyclodecane dimethanol is eluted at a retention time ranging from 12.4 minutes to 13 minutes, the second component is eluted at a retention time ranging from 11.8 minutes to 12.4 minutes, each indicated by elution peaks at respective retention times in a spectrum, and the ratio of the area of elution peaks indicating the second component compared to the area of elution peaks indicating the tricyclodecane dimethanol is between 0.001:1 and 0.04:1.

2. The composition of claim 1, wherein in the gas chromatography, the composition is loaded onto a BP-5 capillary column of 30 meters in length, 530 μm in inner diameter and a film thickness of 1 μm, and characterized with a liquid phase of 5% phenyl and 95% dimethylpolysiloxane and a carrier gas of nitrogen flows at 5 mL/min for an initial minutes followed by a stepping flow rate from 5 mL/min to 10 mL/min at a rate increment of 1 mL/min, under a stepping temperature in a sequence of 50° C. for 1 minutes, then increasing temperature from 50° C. to 180° C. at an increment of 15° C./min, then increasing temperature from 180° C. to 250° C. at an increment of 30° C./min, followed by maintaining 250° C. for 8 minutes, wherein an inlet temperature is 250° C., a sample injection volume of the composition is 2 μL, and a detector is a flame ionization detector operated at 300° C.

3. The composition of claim 1, wherein when characterized in a gas chromatography-mass spectrometry (GC/MS), the second component has a retention time ranging from 15.0 minutes to 16.5 minutes and a fragmentation pattern comprising one or more peaks at mass-to-charge ratio (m/z) comprising 31, 41, 67, 79, 91, 93, 119, 149, 167, or a combination thereof.

4. The composition of claim 3, wherein the fragmentation pattern of the second component comprises peaks at m/z of 31, 41, 67, 79, 91, 93, and 119.

5. The composition of claim 3, wherein the fragmentation pattern of the second component comprises peaks at m/z of 149 and 167 at the retention time ranging from 15.8 minutes to 16.0 minutes.

6. The composition of claim 3, wherein the fragmentation pattern of the second component comprises peaks at m/z of 149 and 167 at the retention time ranging from 16.2 minutes to 16.4 minutes.

7. The composition of claim 3, wherein in the GC/MS, the composition is loaded onto a BP-1 capillary column of 60 meters in length, 320 μm in inner diameter and 1 μm in film thickness, with a liquid phase of 100% dimethylpolysiloxane and a carrier gas of helium, flown at 2 mL/min, under an inlet temperature of 250° C. and operated at a stepping temperature in a sequence of 50° C. for 2 minutes, then increasing temperature from 50° C. to 180° C. at an increment of 15° C./min, then increasing temperature from 180° C. to 250° C. at an increment of 30° C./min, followed by maintaining 250° C. for 6 minutes, and operated with an electron energy of 70 eV, an electron source temperature of 230° C., a quadrupole mass filter temperature of 150° C. and a scan for mass in a range between 20.0 m/z and 230.0 m/z with 0 minute's solvent delay.

8. The composition of claim 3, wherein the tricyclodecane dimethanol has a retention time ranging from 16.5 minutes and 17.5 minutes in the GC/MS.

9. The composition of claim 1, when characterized in the gas chromatography, further comprising a third component which is eluted at a retention time ranging from 10.8 minutes to 11.2 minutes and is indicated by an elution peak at the corresponding retention time in the spectrum, and the ratio of the area of the elution peak indicating the third component compared to the area of the elution peaks indicating the tricyclodecane dimethanol is between 0.00005:1 and 0.005:1.

10. The composition of claim 9, wherein the third component is a compound of formula (X):

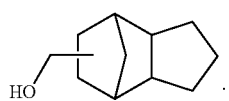

(X)

11. The composition of claim 1, wherein the area of elution peaks indicating tricyclodecane dimethanol compared to a total area of elution peaks of the composition, excluding solvents, is in a ratio of 0.95:1 or greater.

12. The composition of claim 1, wherein the second component is one or a mixture of compounds represented by formula (XI):

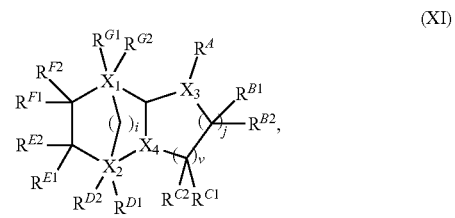

(XI)

wherein,
$X_1$ is C;
$X_2$ is C;
i=1 or 0;
j=1 or 0;
v=1 or 0; and
if i=1, then
  j=v=0,
  $R^{B1}$, $R^{B2}$, $R^{C1}$, $R^{C2}$, $R^{D1}$ and $R^{G1}$ are absent,
  $(X_3-R^4)$ is a linear or branched $C_4$ alkyl alcohol,
  $X_4$ is $CH_2$ or $CH(CH_2OH)$, and
    if $X_4$ is $CH_2$, then
      one of $R^{D2}$, $R^{E1}$, $R^{E2}$, $R^{F1}$, $R^{F2}$ and $R^{G2}$ is $CH_2OH$ whereas the other five of $R^{D2}$, $R^{E1}$, $R^{E2}$, $R^{F1}$, $R^{F2}$ and $R^{G2}$ are H;
    if $X_4$ is $CH(CH_2OH)$, then
      $R^{D2}$, $R^{E1}$, $R^{E2}$, $R^{F1}$, $R^{F2}$ and $R^{G2}$ are H;
if i=0, then
  j=v=1,
  $X_3$ is CH,
  $X_4$ is CH,
  one of $R^4$, $R^{B1}$, $R^{B2}$, $R^{C1}$ and $R^{C2}$ is $CH_2OH$ whereas the other four of $R^4$, $R^{B1}$, $R^{B2}$, $R^{C1}$ and $R^{C2}$ are H,
  one of $R^{D1}$, $R^{D2}$, $R^{E1}$, $R^{E2}$, $R^{F1}$, $R^{F2}$, $R^{G1}$ and $R^{G2}$ is $CH_2OH$, another one of $R^{D1}$, $R^{D2}$, $R^{E1}$, $R^{E2}$, $R^{F1}$, $R^{F2}$, $R^{G1}$ and $R^{G2}$ is $CH_3$, whereas the other six of $R^{D1}$, $R^{D2}$, $R^{E1}$, $R^{E2}$, $R^{F1}$, $R^{F2}$, $R^{G1}$ and $R^{G2}$ are H.

13. The composition of claim 12, wherein the second component comprises one or more compounds of formulae (XI)-(XX):

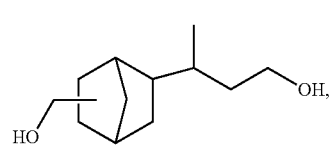

(XI)

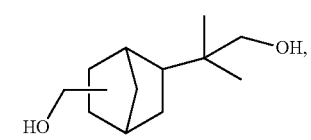

(XII)

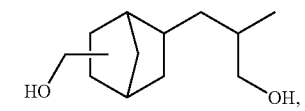

(XIII)

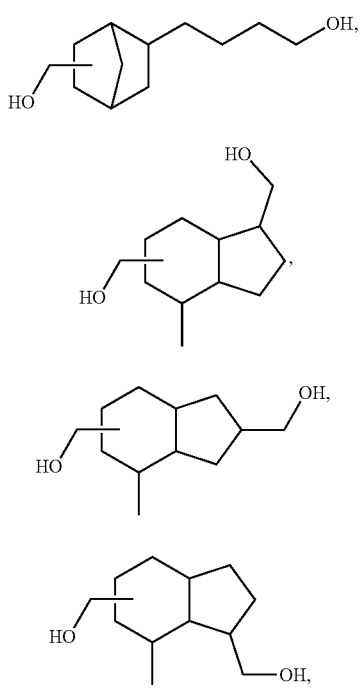
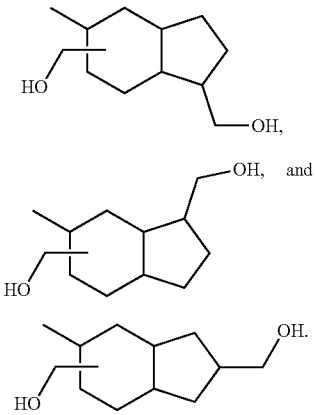
14. A polymer derived from at least the composition of claim 1.
15. The polymer of claim 14, which is a polyester, epoxy, acrylate, polycarbonate or polyurethane derived from at least the composition of claim 1.
16. The polymer of claim 14, which is a polyester derived from at least the composition of claim 1.
17. An optical material comprising the polymer of claim 14.
* * * * *